United States Patent [19]

Allain et al.

[11] 4,216,066
[45] Aug. 5, 1980

[54] PREPARATION OF TETRAMETHYLTIN FROM A MAGNESIUM-TIN ALLOY

[75] Inventors: Ronald J. Allain, Richmond; Joseph P. Maniscalco, Sugar Land, both of Tex.

[73] Assignee: Nalco Chemical Co., Oak Brook, Ill.

[21] Appl. No.: 15,032

[22] Filed: Feb. 26, 1979

[51] Int. Cl.$^2$ ............................ C25B 3/12; C07F 7/22
[52] U.S. Cl. ............................ 204/59 QM; 260/429.7
[58] Field of Search ................ 204/59 QM; 260/429.7

[56] References Cited

U.S. PATENT DOCUMENTS

| 3,028,320 | 4/1962 | Kobetz et al. | 204/59 QM |
| 3,853,735 | 12/1974 | Shepard et al. | 204/260 |

FOREIGN PATENT DOCUMENTS 713727 8/1954 United Kingdom ............... 260/429.7
761357 11/1956 United Kingdom ............... 260/429.7

*Primary Examiner*—F. Edmundson
*Attorney, Agent, or Firm*—John G. Premo; Robert A. Miller

[57] ABSTRACT

A method of producing tetramethyltin which comprises the steps of:

(a) reacting methyl chloride in an ether solvent with a tin-magnesium alloy containing from 1:1 to 1:2 mole ratio of tin to magnesium whereby a substantial quantity of the methyl chloride is converted to tetramethyltin and methyl magnesium chloride, and then (b) electrolyzing the methyl magnesium chloride in an electrolytic cell containing tin anodes whereby additional quantities of tetramethyltin are produced.

1 Claim, No Drawings

PREPARATION OF TETRAMETHYLTIN FROM A MAGNESIUM-TIN ALLOY

INTRODUCTION

Tetramethyltin is a known compound. It can be used as an intermediate to produce tin salts or it can be used as a bactericide or as an anti-foulant in marine paints. It would be beneficial if there were a good method for its production.

THE INVENTION

A method of producing tetramethyltin which comprises the steps of:
(a) reacting methyl chloride in an ether solvent with a tin-magnesium alloy containing from 1:1 to 1:2 mole ratio of tin to magnesium whereby a substantial quantity of the methyl chloride is converted to tetramethyltin and methyl magnesium chloride, and then
(b) electrolyzing the methyl magnesium chloride in an electrolytic cell containing tin anodes whereby additional quantities of tetramethyltin are produced.

EXAMPLES

To illustrate the invention, the following is given by way of examples:

Two six (6) inch electrolytic cells were constructed. One cell was packed with approximately 1200 grams of an alloy made at this lab. The alloy composition had an average 27 wt. percent magnesium and 73 wt. percent tin or a mole ratio of about 2:1, magnesium to tin. The other cell was packed with tin shot (about five pounds). Each cell was equipped with a small centrifugal pump. The system was designed where the cell solution could flow down through a cell to the pump and then to a central surge tank. From the surge tank the solution would flow directly back to the cell. The system was designed where both cells could operate in tandem or separately using the same surge tank. This would allow cell solution from one tank to mix with the cell solution from the other cell.

To begin a run, a 60/40 mixture of tetrahydrofuran/-diethyl ether of tetraethylene glycol solution (1.5 liters) was charged only to the alloy cell. The solution was then circulated over the crushed alloy. Methyl chloride was then added to the flowing solution in an amount equal to about 3–10% of the total solution. This level of methyl chloride was maintained during the entire run. An exothermic reaction would then take place instantly and was controlled by external cooling. A sample analyzed by GC methods indicated that tetramethyltin has been made. Wet method analyses showed also that an active Grignard had been prepared. This tetramethyltin was prepared by a chemical reaction only, not by electrochemical means as in the tetramethyllead process. When the methyl Grignard had reached about one molar strength, the cell solution was allowed to flow into the empty tin shot cell. Both pumps were then operated in tandem allowing the cell solution to flow through both cells equally. The tin shot cell was electrolyzed using a Kepco power supply system. Therefore, the alloy cell produced tetramethyltin and methyl Grignard by chemical reaction while the tin shot cell produced tetramethyltin electrolytically. The two cells could be operated in tandem with both producing tetramethyltin. After a length of time, both cells were emptied and analyses were made.

Using the above technique, the results of several experiments are presented below in Table I.

TABLE I

| RUN | AMP – HRS. | TIN MOLES PRODUCED | % CE[3] | % YIELD BASED on $MgCl_2$ |
|---|---|---|---|---|
| 48-226 | 5.3 | .24 | 500 | 55 |
| 48-228[1] | 0 | .14 | — | 31[2] |
| 48-230 | 12.7 | .14 | 115 | 25 |

$$\% \text{ CE} = \frac{\left(107.2 \frac{\text{amp} - \text{hrs.}}{\text{mole}} \text{ TIN}\right)(\text{TIN MOLES MADE})}{\text{TOTAL AMP} - \text{HRS.}} \cdot 100\%$$

$$\% \text{ YIELD} = \frac{(2 \times \text{TIN MOLES MADE})}{(MgCl_2 \text{ MOLES MADE})} \cdot 100\%$$

[1] Only the alloy cell was operated in this run without electrolysis.
[2] Low yeilds are reflected by the manner of calculation.
[3] Current efficiency

We claim:
1. A method of producing tetramethyltin which comprises the steps of:
(a) Reacting methylchloride in an ether solvent with a tin-magnesium alloy containing from 1:1 to 1:2 mole ratio of tin to magnesium whereby a substantial quantity of the methylchloride present in said ether solvent is converted to tetramethyltin and methyl magnesium chloride, forming thereby a resultant solution of tetramethyltin, methyl magnesium chloride, methyl chloride, and the ether solvent, and then
(b) electrolyzing said resultant solution containing, among its other components, methyl magnesium chloride in an electrolytic cell containing tin anodes whereby additional quantities of tetramethyltin are produced.

* * * * *